United States Patent [19]

Swisher

[11] Patent Number: 5,238,103
[45] Date of Patent: Aug. 24, 1993

[54] CONDOM APPLICATOR

[76] Inventor: Daniel J. Swisher, 230 Spruce Ct., Flemington, N.J. 08822

[21] Appl. No.: 970,156

[22] Filed: Nov. 2, 1992

[51] Int. Cl.[5] .......................................... B65D 85/08
[52] U.S. Cl. ..................... 206/69; 604/349; 128/844
[58] Field of Search .............. 128/844; 600/38–41; 604/349; 206/69; 83/455

[56] References Cited

U.S. PATENT DOCUMENTS

| | | | |
|---|---|---|---|
| 1,726,143 | 8/1929 | Eisinger | 206/69 |
| 2,390,900 | 12/1945 | Schmid | 206/69 |
| 2,567,926 | 9/1951 | Dunkelberger | 128/844 |
| 2,705,951 | 4/1955 | Crowner | 128/844 |
| 2,741,360 | 4/1956 | Harrowe | 206/69 |
| 2,842,238 | 7/1958 | Shaw et al. | 83/455 |
| 3,677,225 | 7/1992 | Czirely . | |
| 4,056,027 | 11/1977 | Northrop | 83/455 |
| 4,484,918 | 11/1984 | Omley | 604/349 |
| 4,738,357 | 4/1988 | Martin et al. . | |
| 4,741,434 | 5/1988 | Liebman . | |
| 4,781,288 | 3/1988 | Wing . | |
| 4,805,820 | 2/1989 | Kearney et al. | 206/69 |
| 4,840,187 | 6/1989 | Brazier . | |
| 4,869,723 | 9/1989 | Harmon | 206/69 |
| 4,875,491 | 10/1989 | Parrone | 206/69 |
| 4,961,734 | 10/1990 | Kassman . | |

FOREIGN PATENT DOCUMENTS

| | | | |
|---|---|---|---|
| 0429144 | 5/1991 | European Pat. Off. | 128/844 |
| 0499098 | 5/1938 | United Kingdom | 206/69 |

*Primary Examiner*—Randall L. Green
*Assistant Examiner*—Gina M. Gualtieri
*Attorney, Agent, or Firm*—Kenneth P. Glynn

[57] ABSTRACT

The present invention is directed to a condom applicator device which includes a top encasement and a bottom encasement which are hingedly connected to one another. The top and bottom encasements include orifices of adequate diameter for an erect penis to pass through and either the top encasement or the bottom encasement or both includes a blade or blades which are located strategically with respect to the orifices within both encasements such that the top and bottom encasements can be opened with respect to one another, a condom package in a foil inserted therein, and, when encasements are closed, the blade or blades cut through the condom foil without touching the condom itself. The top foil may then be simply pulled away when ready for use and the bottom foil is taken away by a bottom hatch door which is hingedly attached on the underside of the bottom encasement. Once the condom foil has been removed from both the top and the bottom, a user may simply hold the device and pass an erect penis therethrough so as to unroll and apply the condom.

11 Claims, 3 Drawing Sheets

CONDOM APPLICATOR

BACKGROUND OF THE INVENTION

1. Field of the Invention

The present invention is directed to a condom applicator. More specifically, is directed to a device for storing, piercing the foil wrap of a condom, and applying a condom to an erect penis without the need for direct contact and possible contamination of the condom itself by the user.

2. Information Disclosure Statement

Condoms have been available for many decades and have been used prudently by couples to prevent pregnancy as well as to avoid what are commonly known as social diseases. However, with the advent of the problems resulting from HIV positive and the AIDS disease, the use of prophylactic products have substantially increased. Further, there seams to be a need for a more sanitary approach to the application of the condom itself, as well as a more socially acceptable method of carrying and using condoms. Thus, the present invention is directed to an applicator which may be used by the male or female in which may be used as a temporary carrying case as well.

Numerous condom applicators have been developed over the years but none which provide for the sanitary and storage advantages of the present invention.

U.S. Pat. No. 3,677,225 issued to Julius Czirely, describes a contraceptive device which includes an annular handling device which is stripable attached to the exterior of the container to facilitate handling prior to enduring the application of a contraceptive device.

U.S. Pat. No. 4,738,357 issued to Claus Martin, et al. describes an element for receiving a condom which includes an angular ring U.S. Pat. No. 4,741,434 describes a keyholder with an attached condom case which includes a two component member and means for attaching to a keychain or the like.

U.S. Pat. No. 4,781,288 sets forth a hermetically sealed flat case for storing prophylactics but does not provide for the device being used for application thereof.

U.S. Pat. No. 4,840,187 issued to Gary Brazier, describes a sheath applicator which relies upon the use of a tubular applicator and the netting liner located in the applicator casing and secure to a closed end. The penial sheath for condom is located inside the liner casing and the open end of the casing is folded back over the casing so that it can be opened and used for application.

U.S. Pat. No. 4,961,734 describes an accordion type applicator which relies upon expansion of the applicator for direct application of the condom.

U.S. Pat. No. 4,875,491, describes a condom holder device but this device is for application of a ring with holding straps to the body as to prevent the condom from sliding off the penis during erection and intercourse. It is also designed so as to secure the condom to the human body with only a single hand without interruption of activity, as states therein.

Notwithstanding the prior art sighted, there is no teaching or suggestion to render obvious the present invention wherein an encasement in used to carry the condom, cut the condom seal, and be utilized for direct application of the condom to the erect penis without contact by the user.

SUMMARY OF THE INVENTION

The present invention is directed to a condom applicator device which includes a top encasement and a bottom encasement which are hingedly connected to one another. The top encasement and the bottom encasement include orifices of adequate diameter for an erect penis to pass through and either the top encasement or the bottom encasement or both includes a blade or blades which are located strategically with respect to the orifices within the top and bottom encasements such as the top and bottom encasements can be opened with respect to one another, a condom packages in a foil inserted therein, and, when encasements are closed with respect to one another, the blade or blades cut through the condom foil without touching the condom itself. The top foil may then be simply pulled away when ready for use and the bottom foil is taken away by a bottom hatch door which is hingedly attached on the underside of the bottom encasement. Once the condom foil has been removed from both the top and the bottom, a user may simply hold the device and pass an erect penis therethrough so as to unroll and apply the condom.

BRIEF SUMMARY OF THE DRAWINGS

The present invention will be more fully understood and appreciated when the disclosure herein is taken in conjunction with the drawings appended hereto, wherein.

DETAILED DESCRIPTION OF THE INVENTION AND DRAWINGS

The present invention is directed to a condom applicator device which includes a top encasement and a bottom encasement which are hingedly connected to one another. The top encasement and the bottom encasement include orifices of adequate diameter for an erect penis to pass through and either the top encasement or the bottom encasement or both includes a blade or blades which are located strategically with respect to the orifices within the top and bottom encasements such as the top and bottom encasements can be opened with respect to one another, a condom packages in a foil inserted therein, and, when encasements are closed with respect to one another, the blade or blades cut through the condom foil without touching the condom itself. The top foil may then be simply pulled away when ready for use and the bottom foil is taken away by a bottom hatch door which is hingedly attached on the underside of the bottom encasement. Once the condom foil has been removed from both the top and the bottom, a user may simply hold the device and pass an erect penis therethrough so as to unroll and apply the condom.

Figure 1:
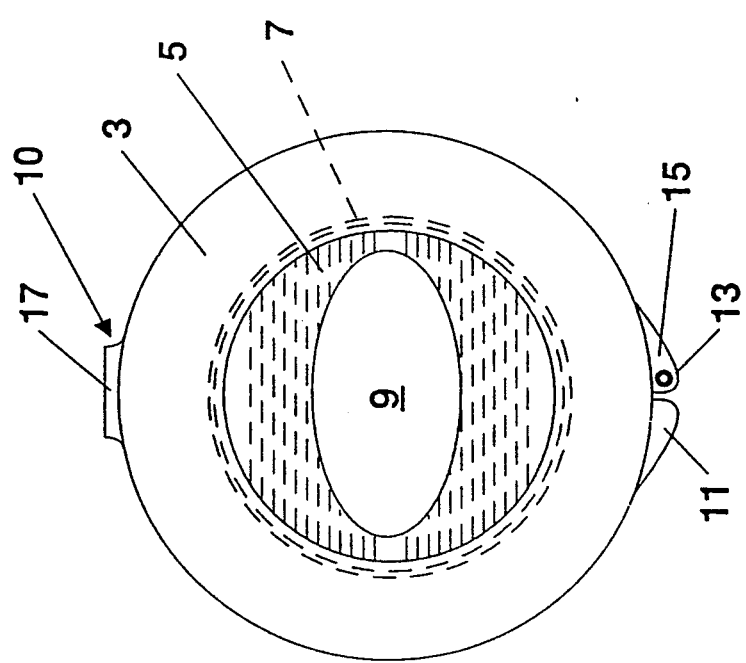
FIG. 1 shows a top view of a first embodiment of a present invention having a round case configuration.

Referring more specifically now to FIG. 1, there is shown a top view of a present invention embodiment condom applicator device 10. As can be seen, device 10 has a round configuration, although it could be square, rectangular, hexagonal or otherwise without exceeding the scope of the present invention. There is a top encasement 3 and a bottom encasement (not shown) which is hingedly connected to top encasement 3 by a hinge means 17. Top encasement 3 has blades shown by a dotted circle 7 such that when foil wrapped condom 9 in inserted into device 10 and top encasement 3 is shut to the bottom encasement by snaps such as snaps 13 located on snap ledge 15 and a snap on the underside of snap ledge 11, blade 7 cuts through the foil but is of greater diameter of the condom contained within the foil so that the foil is cut and the condom is not cut. The foil top of the condom package 9 is removed from top encasement orifice 5, the top of the condom is exposed. Likewise, when the bottom foil if removed through a bottom encasement orifice (not shown) the condom is now open on both sides.

Device 10 may next simply be place atop an erect penis and as the penis passes through the orifices of device 10, the condom unrolls and is applied. Once it is fully unrolled, then device 10 may simply be removed by upward movement.

The hinge mechanism 17 as well as snap ledges 11 and 15 and snap 13 are well within the skill of the artisan and need not be described in detail. It would be sufficient to say that any conventional closure mechanism such as snap 13 and any conventional hinge mechanisms may be utilized. Thus, the typical snap mechanisms for cases such as for eyeglasses, makeup compacts, birth control pills and the like may be utilized.

Although not shown in FIG. 1, device 10 could be included in another encasement or partial encasement to provide for long term storage of a condom (e.g. a number of days or a week or so) but in its configuration with the open orifice 5, once the device 10 is closed and blade 7 cuts through the foil pack it is important that the condom be utilized with a short period of time to prevent its effectiveness and prevent its drying out.

Figure 2:
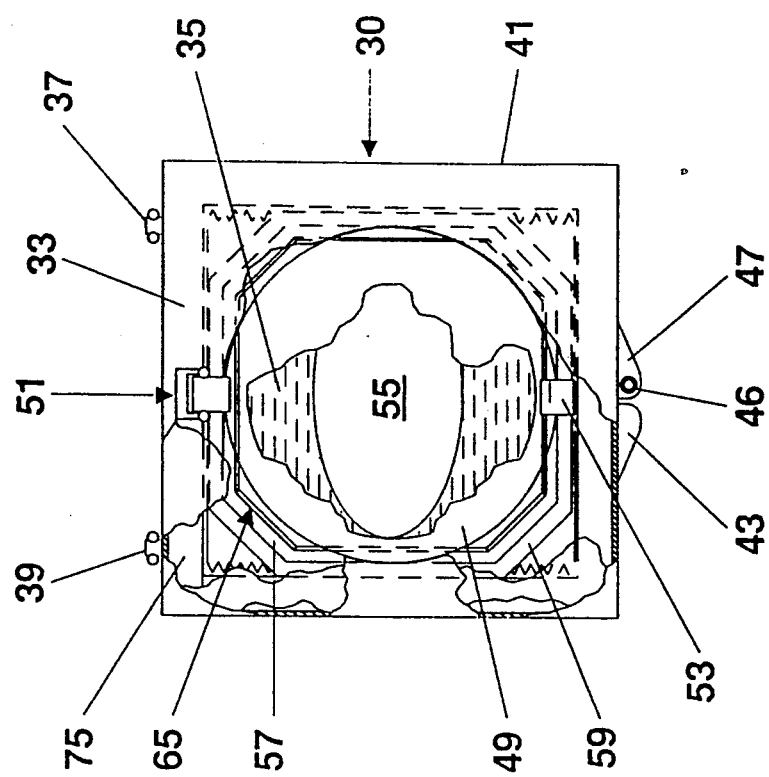
FIG. 2 shows a top partially cut view of a second embodiment of the present invention using a square case configuration as well as a cover or hatch door on the top orifice; and, FIGS. 3, 4 and 5 respectively show a left side cut view, a front cut view and a bottom cut view of the device shown in FIG. 2.
Figure 3:
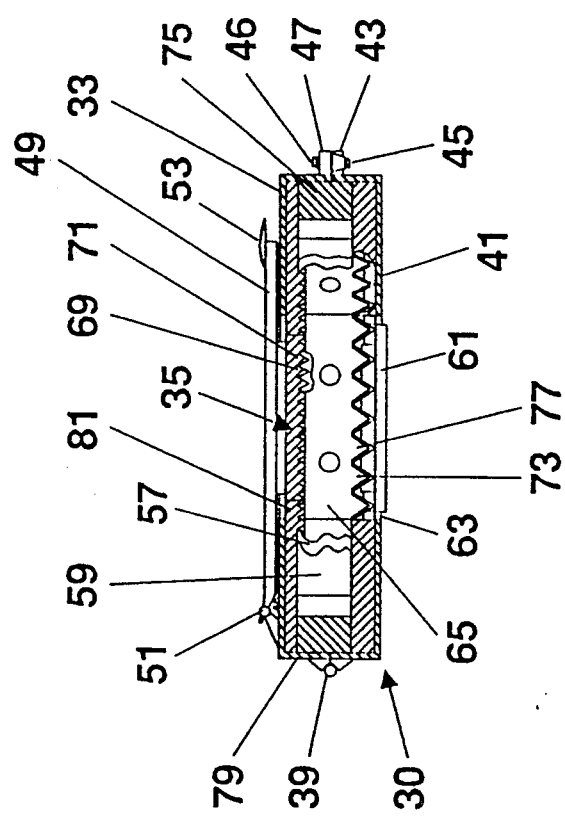
Figure 5:
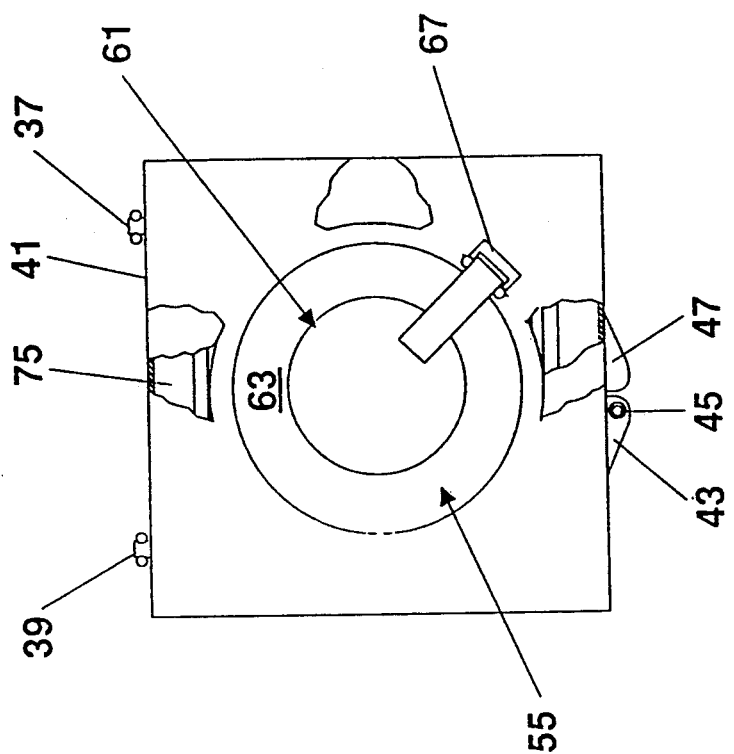
Figure 4:
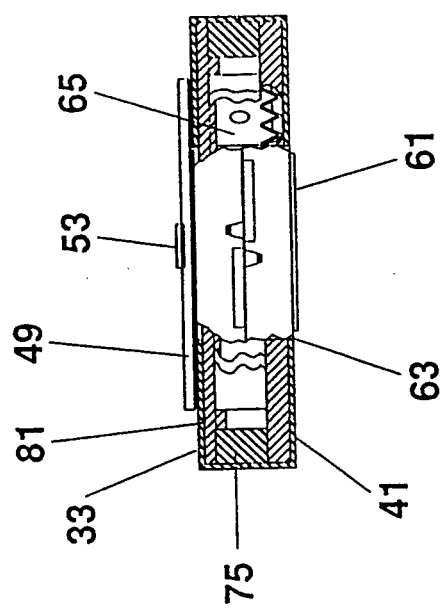

Referring now to FIG. 2, there is shown a second embodiment present invention device 30 in its top, partial cut view. FIGS. 3, 4 and 5 respectively show a left side view, a front view and a bottom view with a partial cutout of the device 30 shown in FIG. 2. Thus, the following descussion will shall be in reference to FIGS. 2, 3, 4, 5 collectively.

Present invention condom applicator device 30 includes a top encasement 33 having a top orifice 35 a bottom encasement 41 and a bottom encasement orifice 63. Top encasement 33 and bottom encasement 41 are connected in a hinged fashion by hinges 37 and 39, as shown. Closure is fixedly completed by means of snap 45 located on snap ledge 43 and snap 46 located on ledge 47.

There is an optional top hatch door 49 having hinge 51 which is a two position hinge which connects it to top encasement 33. This two position hinge 51 has a spring type force so that it is held in a first, closed position and, when opened up, stays in an open, upward position such as at an angle of 90°, 120° or the like. It is held closed by way of force fit or snap latch 53. When top encasement 33 is opened relative to bottom encasement 41 and a condom such as condom package 55 is inserted therein, the condom is held in place by a condom holder frame 75 and also by ribs such as ribs 69 and 71.

It should be noted that the top encasement 33 and bottom encasement 41 has side walls such as side wall 79, however, either one may have an extended side wall to meet a flush opposite encasement. However, the arrangement of having both the top and bottom encasement with side walls that meet in a flush fashion when closed is preferred. To eliminate a side wall connection to one or the other of the top or bottom encasement, however, would not exceed the scope of the present invention. Further, the device 30 includes a pad 81 which is located on the underside of the top encasement 33 and would have the top orifice pass there through. Such pad would optionally include ribs such as ribs 69 and 71 and a similar arrangement could be used in the bottom encasement.

There is a blade 65 with respect to device 33 which is attached to top encasement 33 so that when top encasement 33 is opened and a condom package inserted, and then top encasement is closed, the blade 65 cuts throught the condom package but not the condom itself alternatively, the blade could be connected to the bottom encasement 41 or there could be blades connected to both the top and bottom encasement. The critical feature is that there is at least one blade and that the blade closes down upon or closes up upon a foiled condom package. The blade as shown in FIG. 1 was circular in configuration. However, the blade for present invention device 30 is, as shown by FIG. 2, of an eight sided configuration, i.e. somewhat square with cutoff corners. The exact configuration is not critical as long as the blade cuts through the foil completely or almost completely so that it can be easily removed while not cutting through or in any way damaging the condom within the foil.

Within device 30 is a blade holder 57 and a blade safety guard 59. The safety guard protects the blade 73 and 77 from doing any damage or harm to the condom or to an erect penis or to the holder because once device 30 is closed, the blades are encased within blade safety guard 59 and are unable to come into contact with anything else.

FIG. 5 shows a bottom view and here bottom hatch door 61 is connected to position bottom hinge 67. Thus, once the device 30 has been closed with a condom package such as condom package 55 contained therein, when the condom is ready to be used, the user will flip open bottom hatch door 61 and physically remove the bottom foil. In the alternative, bottom hatch door 61 may include adhesives as to stick to the foil of condom package 55 and, in this instance, when hatch door 61 is opened, the bottom foil which is now cut is readily removed to expose the condom contained therein. Likewise, there is a top hatch door 49 with hinge 51 which is opened by latch 53 so that the user may remove the top cut foil portion of condom 55. Alternatively, top hatch door 49 may likewise contain adhesive to remove the foil automatically upon opening.

Once the hatch doors are opened and the foil removed, the user may simply hold the device and pass an erect penis therethrough so as to unroll and apply the condom. Again, the device is then removed by upward movement with the condom being applied without ever having being touched by the male or female involved.

It can now be seen that the present invention provides for a short term carrying case device as well as a device for removing foil from a foil wrapped condom and, additionally, providing for sanitary and direct application of the condom without it ever being touched by the user of the applicator and, in the case were someone other than the person upon which the condom is applied, neither party needs to touch the condom with the hands in order to apply it for use.

Obviously, numerous modifications and variations of the present invention are possible in light of the above teachings. It is therefore understood that within the scope of the appended claims, the invention may be practiced otherwise than as specifically described herein.

What is claimed is:

1. A condom applicator device, which comprises:
   (a) a top encasement having an orifice therein, said orifice being a top encasement orifice having a periphery and a predetermined diameter adapted to freely pass an erect penis therethrough;
   (b) a bottom encasement having an orifice therein, said bottom encasement orifice having a periphery and having a predetermined diameter adapted to freely pass an erect penis therethrough,
   (c) hinge means connecting said bottom encasement and said top encasement so as to align said top encasement orifice and said bottom encasement orifice and so as to hingedly connect said top encasement and bottom encasement so as to enable said encasement to be opened and closed relative to one another;
   (d) at least one blade located on either of said top encasement or said bottom encasement around the periphery of said encasement orifices such that when a foil wrapped condom is placed in said device, and when said top encasement and said bottom encasement are closed with respect to one another, said one or more blades penetrates the encasement space opposite said blade sufficiently so as to cut through said foil of said foil wrapped condom;
   (e) a bottom encasement hatch door located within said bottom encasement orifice; and
   (f) hinge means connected to said bottom encasement hatch door so as to enable said door to be positioned in a first position within said bottom encasement orifice and a second position approximately 90 degrees or greater away from said bottom encasement orifice.

2. The device of claim 1 wherein at least one of said top encasement and bottom encasement have side walls which include a condom holder frame having a configuration for holding a foiled wrapped condom within said device in alignment with said top encasement orifice and said bottom encasement orifice and said at least one blade.

3. The condom applicator device of claim 1, wherein either one or both of said top encasement and said bottom encasement further includes ribs for clamping down on a foil wrapped condom when said bottom encasement and said top encasement are closed with respect to one another.

4. The device of claim 1 further comprising means for fixedly closing said top encasement and said bottom encasement with respect to one another.

5. The device of claim 1 wherein a single continuous band blade is utilized which covers the entire periphery of said orifice so as to cut foil wrapper of a condom and so as to not cut the condom itself.

6. The device of claim 5 wherein said at least one blade is a teethed blade.

7. The device of claim 1 wherein said at least one blade is a teethed blade.

8. The device of claim 1 wherein said top encasement and said bottom encasement have a circular shape, said shape being concentric with said orifice.

9. The device of claim 1 where in said top encasement further includes a top hatch door and hinge means connecting said hatch door to said top encasement wherein said hatch door covers said top encasement orifice.

10. The device of claim 9 wherein said hinge means has a first position which corresponds to a closed position and a second position which corresponds to an open position of approximately 90 degrees or more away from said top encasement.

11. The device of claim 1 wherein said bottom hatch door includes adhesive means on a surface facing the top encasement, and, when a foil wrapped condom is placed in said device, said adhesive means adheres to a portion of the foil of a foil wrapped condom located therein.

* * * * *